United States Patent
Ponzin

(12) 
(10) Patent No.: US 6,838,448 B2
(45) Date of Patent: *Jan. 4, 2005

(54) CORNEAL STORAGE FLUID COMPRISED OF HYALURONIC ACID

(76) Inventor: Diego Ponzin, Via Pioveghetto 15 35136, Padova (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 134 days.

(21) Appl. No.: 09/155,675
(22) PCT Filed: Apr. 4, 1997
(86) PCT No.: PCT/EP97/01703
§ 371 (c)(1), (2), (4) Date: Dec. 2, 1998
(87) PCT Pub. No.: WO97/37537
PCT Pub. Date: Oct. 16, 1997

(65) Prior Publication Data
US 2001/0009908 A1 Jul. 26, 2001

(30) Foreign Application Priority Data
Apr. 4, 1996 (IT) .......................... 96A000084

(51) Int. Cl.⁷ .................. A61K 31/715; C08B 37/00
(52) U.S. Cl. ............................................. 514/54; 536/53
(58) Field of Search ................................ 514/54; 536/53

(56) References Cited

FOREIGN PATENT DOCUMENTS

| EP | 0138572 | 4/1985 |
|---|---|---|
| EP | 0197718 | 10/1986 |
| EP | 0517972 | 12/1992 |
| JP | 6-107538 | * 4/1994 |

OTHER PUBLICATIONS

Translation of JP 6–107538, Apr. 1994, Shiseido Co Ltd, provided by Applicant with the reposne of Jul. 13, 2003.*
Fortschr. Ophthalmol., vol. 88, No. 2, Apr. 1991, pp. 113–117, M. Bohme, M. Hagenah & J. Draeger.
Database WPI, Section Ch., Week 9420, Derwent Publications Ltd., London, GB; AN 94–163841, JP6107538, Apr. 19, 1994.

* cited by examiner

Primary Examiner—Kathleen K. Fonda
(74) Attorney, Agent, or Firm—Birch, Stewart, Kolasch & Birch, LLP

(57) ABSTRACT

A solution for storing corneal tissue, especially at a temperature of 2 to 8° C., which comprises hyaluronic acid having an average molecular weight of less than 6,000,000 Da (preferably of from 50,000 to 250,000 Da).

6 Claims, No Drawings

US 6,838,448 B2

CORNEAL STORAGE FLUID COMPRISED OF HYALURONIC ACID

The present application is the U.S. national stage application under 35 U.S.C.§371 of PCT/EP97/01703, having an International filing date of Apr. 4, 1997.

OBJECT OF THE INVENTION

The aim of the present invention is to improve and simplify the storage of corneas destined for penetrating keratoplasty in the time between removal from the donor and transplantation, by the use of storage fluid formulations containing hyaluronic acid

BACKGROUND AND FIELD OF THE INVENTION

Penetrating keratoplasty is widely used to restore vision in a number of corneal illnesses. In severe corneal dystrophy, inflammation or degenerative processes, penetrating keratoplasty is the only effective therapy to obtain visual rehabilitation. A major issue in this therapy is the method used to preserve a viable corneal tissue after its removal from the donor.

The cornea is an avascular tissue with a well defined organization, 1 mm thick peripherally and 0.5 mm thick centrally. The part exposed to the external environment is covered by a stratified, nonkeratinized epithelium formed by 3 to 4 layers of flattened squamous cells, 1 to 3 layers of midepithelial cells and a single layer of columnar basal cells attached to the basement membrane and the underlying stroma by an adhesion complex. During corneal storage, epithelium may be lost but if the basement membrane is undamaged, re-epithelialization after the transplant is usually rapid. The stroma is arranged in three distinct layers of extracellular matrix. Starting from the epithelium, these include a thin Bowman's layer, a middle lamellar stroma and a basement membrane (Descemet's membrane) that is generated by the endothelial cells lining the side of the tissue facing the aqueous humor. The other parts of the stroma are produced and maintained by the stromal fibroblasts, flat cells commonly termed keratocytes.

Because of the presence of salts, collagen and proteoglycans, the stroma is hypertonic with respect to both tears and aqueous humor. Water is less concentrated in the epithelial side likely because of drying through the epithelium layers. Similarly, glucose is less concentrated in the epithelial side because this metabolite flows from the aqueous humor to be largely utilized by the epithelium. The stroma contains proteoglycans (dermatan and keratan sulfate) with the former more concentrated in the epithelial side and the latter in the endothelial side. The corneal endothelium is a single layered, cuboidal endothelium forming a hexagonal mosaic lying on Descemet's membrane when viewed from the anterior chamber. The hexagonal cells are linked together by tight junctions which, however, do not form a complete seal around the cells. Rather, they are concentrated in the cell apical membrane. Junction integrity depends on the presence of Ca2+ in the surrounding medium. This organization allows the aqueous humor and its solutes to have access to the paracellular space. Under normal conditions, fluid influx is not followed by the swelling of cornea because an equivalent volume of fluid is actively removed by the pumping complex of the endothelium. The Na+-K+ ATPase is an essential part of this pumping system which therefore requires the ATP produced by the metabolic activity of endothelial cells.

To fully evaluate the function of endothelial cells, it is of interest to observe that these cells have, on the side facing the aqueous humor, the immunoglobulin family member, ICAM-1 (intercellular adhesion molecule-1), which serves as a coreceptor for the integrin LFA-1 ($\alpha$ L, $\beta$2), located in the leukocyte surface. ICAM-1 may also function as a receptor for hyaluronic acid (McCourt, P. A. G. et at. (1994) J. Biol. Chem. 269, 30081–30084). This indicates that endothelial cells interact with leukocytes when they reach the aqueous humor. It may also indicate that under normal conditions and in the absence of leukocytes, hyaluronic acid associates with this receptor to preserve the integrity of the endothelial layer.

Swelling of corneas: When the pumping function of the endothelium is lost, hypertonicity of stroma causes the corneal tissue to swell. Swelling results in the increase of corneal thickness and a decrease in clarity. Furthermore, there is a loss of proteoglycans from the stroma to the surrounding medium. Loss of endothelial function is the consequence of pathological events (e.g. dystrophies, degenerations, glaucoma). Aging may favor endothelial decompensation since the number of endothelial cells declines with age (about 50% from birth to old age). Since endothelial cells have limited regenerative capacity, damage to the endothelium integrity can only be compensated by the enlargement of residual cells which become thinner. Endothelial damage is also the major risk in the storage of corneas before transplantation. This event results in corneal swelling with loss of clarity and progressive endothelial cell death. Preservation of an intact endothelial layer is, indeed, a major goal in devising methods to preserve corneas before penetrating keratoplasty.

Storage of corneas: Whole ocular globes from donors can be stored in a moist chamber at 4° C., but should be used within 24 h. Preservation of corneas in the frozen state has been successfully exploited (Kaufman, H. E. and Capella J. A. (1968) J. Cryosurg. 1, 125–129). Before freezing, corneas are treated with increasing concentrations of DMSO and sucrose to prevent formation of intracellular ice. Difficulties in handling and transport of frozen corneas at a constant low temperature prevent the diffusion of this technique. Alternatively, corneas can be stored at 37° C. in organ culture medium (Doughman D. J. et al. (1976) Trans. Am. Acad. Ophtalmol. Otolaringol. 81, 778–793). Since culture media are supplemented with serum for optimal cell preservation, this method has the disadvantage of exposing the recipient eye to a residual amount of serum transported by the cornea at the moment of transplant. Animal serum may elicit an immune response while human serum may transmit viral diseases.

At present, the most convenient method for corneal preservation appears to be short-term storage in serum-free media at 4° C. At this temperature, the metabolic activity of endothelial cells is minimal. Thus, pumping function is lost.

Cornea swelling may be prevented by the addition of water-retentive compounds to the preservation medium. Among these, one of the most used is the deturgescent compound, dextran, either alone (McKarey, B. B. and Kaufman, H. E. (1974) Invest. Ophthalmol. Vis. Sci. 13, 165) or in association with the glucosaminoglycan chondroitin sulfate (Kaufman H. E. et al. (1991) Arch. Ophthalmol. 109, 864–868). However, chondroitin sulfate is a heterogeneous compound because of the varied distribution of the sulfate molecules within the polymer (Scott, 1995). As a result, the compositions to be used for corneal storage may vary between lots. In addition, due to the sulfate molecules, chondroitin sulfate carries a strong negative charge.

It has recently been suggested that this strong negative charge is detrimental to corneal preservation because the strong negative charges decrease the adhesion capability of corneal endothelium (Chen et al. 1996). Further, it has been reported that chondroitin sulfate can penetrate the cornea and favor its swelling, particularly upon rewarming the tissue from 4° C. to room temperature, before transplant (Kaufman et al. 1991). In an attempt to decrease the corneal swelling induced by chondroitin sulfate, cornea preservation compositions were formulated which contain deturgescent agents such as dextran, in combination with chondroitin sulfate (EP 0 517 972). However, dextran may penetrate the stroma during storage and may increase the swelling pressure on rewarming. In addition, it is now also clear that dextran can be toxic to the cornea, inducing senescence and degeneration (Chen et al. 1996).

Ogino et al. (Mokugan Zen-shi, Effect of a Newly Developed Corneal Storage Medium on Corneal Endothelium—Morphological Study by Scanning Electron Microscopy, 1995) describe a storage medium containing hyaluronic acid (HA). But the hyaluronic acid utilized by Ogino et al. had a molecular weight of 800,000. Such a high molecular weight HA is too viscous to be suitable as a storage medium component and must be used in combination with some other water-retaining component to prevent cornea swelling without augmenting the viscosity of the solution.

It is, therefore, an object of the present invention to provide a cornea storage fluid capable of providing suitable storage conditions for viable cornea, while avoiding the drawbacks of prior fluids.

DETAILED DESCRIPTION OF THE INVENTION

The present invention is, therefore, directed to a cornea fluid composition comprised of hyaluronic acid, and the use of a formulation comprised of hyaluronic acid which is suitable for the preservation of viable cornea at low temperatures, especially between 2–8° C. The invention is based on the following assumptions, which are in line with the considerations on corneal organization and function, discussed above:

(i) During storage of corneas at low temperatures, the metabolic activity of endothelial cells is silent. Thus, nutrients and growth factors (serum or others) are not needed. Pumping function is not performed and does not need support.

(ii) A balanced saline solution supplemented with a water-retaining compound should be sufficient to maintain cornea integrity. If a single water-retaining compound is appropriate other compounds such as dextran are no longer necessary.

(iii) A protective film above the endothelial cells is required to prevent them being damaged during storage. A natural ligand able to associate with the core-ceptor ICAM-1 seems suitable.

As outlined below, we have identified HYALURONIC ACID as the appropriate compound fulfilling the requirements for optimal cornea storage at low temperatures.

Hyaluronic acid belongs to the group of glycosaminoglycans which also includes compounds containing sulfate groups (chondroitins, keratans and the heparans). As a consequence of variable distribution of sulfate residues, this group of glycosaminoglycans is an heterogeneous assemblage of different molecules. By contrast, hyaluronic acid only contains the disaccharide unit N-acetyl glucosamine and glucuronate. Thus, hyaluronic acid is a homogeneous compound with a definite primary structure: straight chains containing hundreds of disaccharide units and hundreds of anions fixed to each chain (the carboxylate groups).

Recently, an ordered second structure has been identified in hyaluronic acid (Scott, J. E. (1995) Eur. J. Rheumatol. Inflamm. 15, 3–8). This is supported by extensive hydrogen bonds between the sugar units and a two-fold helix structure caused by a 180° twist between the disaccharide units. The secondary structure yields extensive hydrophobic patches in the hyaluronic acid chains of about 8 CH units (the length of a short chain fatty acid), which are able to associate with the membrane phospholipids or other lipids. Indeed, the beneficial effect of hyaluronic acid in inflamed joints may be the result of its association with lipid-like inflammatory cytokines such as platelet activating factor.

At dilute concentrations of hyaluronic acid in aqueous media (1 $\mu$g/ml or more), a tertiary structure is formed (Scott, J. E. et al. (1991) Biochem. J. 274, 699–705). This is a honeycomb-like meshwork formed by the aggregation of the hyaluronic acid chains establishing a dynamic contact among all hyaluronic acid molecules. The meshwork traps inside water and solutes, thus restricting their interaction with the external environment. Cells with receptors for hyaluronic acid can anchor extensive meshwork around themselves. This may have a protective effect since chemicals are prevented from approaching the cells. Of interest is the observation that this organization becomes less compact and may actually be disrupted by the action of OH free radicals which induce degradation of hyaluronic acid chains. In conclusion, the properties of hyaluronic acid relevant to the present invention and for the purpose of maintaining a viable cornea are as follows:

1. The presence of fixed anions in the hyaluronic acid chains, functioning as a soluble cation exchanger and therefore limiting the movement of monovalent and divalent cations toward the corneal tissue.
2. The presence of hydrophobic patches in the secondary structure of hyaluronic acid chains allowing the compound to contact and protect hydrophobic sites possibly exposed in the cell membrane.
3. The formation of a network by the hyaluronic acid chains enclosing water and solutes and producing maximal water-retentive effect.
4. The interaction with ICAM-1 located on the surface of endothelial cells ensuring the formation of a protective film of hyaluronic acid around the cells themselves.

In principle, these properties are sufficient to obtain the preservation of endothelial cells at low temperatures and to avoid corneal swelling. Since hyaluronic acid of high molecular weight (1,000,000 Daltons or more) forms viscous solutions, lower molecular weight hyaluronic acid should be used. In particular, the hyaluronic acid should have an average molecular weight of less than about 600,000, preferably have an average molecular weight within the range of 50,000 to 250,000 Daltons, most preferably within the range of 50,000 to 150,000 Daltons. At this molecular size, a hyaluronic acid meshwork is still formed, although the organization may be less compact.

For the medical solutions encompassed by the present invention, hyaluronic acids may be obtained from several sources. For example, hyaluronic acid may be purified from conventional sources such as rooster combs using the processes described in EP 0 138 572. Alternatively, hyaluronic acid may be obtained through a fermentation process as described in WO 95/04132 or by enzymatic synthesis using a purified protein factor containing hyaluronate synthase, as described in WO 95/24497.

FORMULATION EXAMPLES

The serum-free medical solution proposed in the present invention should contain:

1. A balanced electrolyte solution buffered at pH 7.2–7.4 with phosphate, bicarbonate and Hepes (hydroxyethylpiperizine ethanesulfonic acid). For purposes of the invention, a minimal essential medium (e.g. TC 199 such as obtainable from Gibco BRL, Maryland; Signa, Missouri; Flow Laboratories, Maryland) is satisfactory. This medium is widely used in tissue culture and contains, in its formulation, essential inorganic salts, amino acids, vitamins and ATP precursors.
2. Antibiotics such as, but not limited to, gentamycin, streptomycin, penicillin G and combinations thereof, to prevent microbial contaminations.
3. Hyaluronic acid sodium salt with a molecular weight of 50,000–150,000 Da, added at a 1 to 20 mg/ml, 0.1 to 2% wt/vol., based on the total solution.

Variation can be made in the choice of saline buffered solution and of antibiotics. This simple composition should be sufficient to fulfil all requirements for optimal corneal storage at low temperatures for at least a week.

BIOLOGICAL EVALUATIONS

1. Materials and Methods

The serum-free medium composition comprised of hyaluronic acid sodium salt is described in Table I, in comparison with commercially available corneal storage media containing chondroitin sulfate and dextran (Optisol-GS) or dextran alone (McKarey-Kaufman).

Paired human donor eyes were removed within 9–10 hours of death. Corneas were isolated from the globes with a 2 mm scleral rim and tested for endothelial cell viability, endothelial cell density, corneal thickness and clarity. Endothelial cell viability was assessed by staining with 0.3% trypan blue. Cell death usually distributes in two patterns: regular arrays of stained cells corresponding to folds produced by mechanical stress of corneas during removal and a diffuse mortality indicative of metabolic dysfunction of the endothelial cells. The analysis was completed at the end of each experiment by staining with Alizarin red to evaluate cell morphology and the areas of Descemet's membrane not covered by the endothelium. Cell death was expressed as percent of stained cells with respect to the total cells. Endothelial cell density was evaluated counting the cells in 5 fields of the central part of the corneas using an optical microscope fitted with a 10×10 mm square graticule. When cell death was less than 2% and the number of endothelial cells was >2000 mm2, corneas were considered suitable for transplantation. Corneal thickness was measured by means of an upright microscope fitted with a digital micrometer to evaluate the distance between the epithelium and the endothelium. Three central readings were obtained for each cornea. Clarity was evaluated with an upright microscope and graded as follows; grade 3, excellent; grade 2, good with some irregularity in Descemet's membrane; grade 1, unsatisfactory because of stromal edema or pronounced irregularities in Descemet's membrane. After the analysis, corneas were immersed in the storage medium at 4° C. for subsequent tests of preservation or use for penetrating keratoplasty.

In vitro studies: These experiments were performed with well preserved donor corneas unsuitable for transplantation because of donor contraindications or disease.

Paired human donor eyes were removed within 10 hours of death. Corneas were isolated from the globes with a 2 mm scleral rim and tested for endothelial cell viability, endothelial cell density, corneal thickness and clarity. Endothelial cell viability was assessed by staining with 0.3% trypan blue. Cell death usually distributes in two patterns: regular arrays of stained cells corresponding to folds produced by mechanical stress of corneas during removal and a diffuse mortality indicative of metabolic dysfunction of the endothelial cells. The analysis was completed at the end of each experiment by staining with Alizarin red to evaluate cell morphology and the areas of Descemet's membrane not covered by the endothelium. Cell death was expressed as percent of stained cells with respect to the total cells. Endothelial cell density was evaluated counting the cells in 5 fields of the central part of the corneas using an optical microscope fitted with a 10×10 mm square graticule.

Cell death above 10% and clarity of grade 1 were considered to be incompatible with the experiment. Corneal thickness was measured by means of an upright microscope fitted with a digital micrometer to evaluate the distance between the epithelium and the endothelium. Three central readings were obtained for each cornea. Clarity was evaluated with an upright microscope and graded as follows: grade 3, excellent; grade 2, good with some irregularity in Descemet's membrane; grade 1, unsatisfactory because of stromal edema or pronounced irregularities in Descemet's membrane. After the analysis, corneas were stored in 10 ml of the test medium (either hyaluronic acid sodium salt, Optisol-GS or McKarey-Kaufman) at 4° C. for 7–14 days.

Clinical Studies. An uncontrolled, open-label study was conducted with corneas evaluated as described above, and stored in the medium containing hyaluronic acid. Corneas stored in Optisol-GS medium served as a control. Donors were 46 to 86 years old. Their corneas, collected between 2 and 9 hours from death, were in excellent condition of preservation as judged from clarity, thickness, endothelial cell viability (lack of trypan blue positive cells) and density (2200–3000 cells/mm$^2$). The time of storage at 4° C. was 25–96 hours (see Table 2). Corneas were warmed to room temperature at the time of transplantation. A total of 16 recipients were admitted, requiring penetrating keratoplasty for keratoconus, bullous keratopathy, Groenow dystrophy, acquired endothelial dystrophy, and leukomas. Operative and postoperative care were the same in all cases. Two weeks from the transplant the extent of re-epithelialization, the corneal clarity, the thickness (measured by an ultrasonic pachimetry) and the endothelial cell density (evaluated by fixed-frame analysis of specular photographs) were recorded. The patients were further examined after two months.

2. Results

In vitro studies: Five pairs of corneas were stored in either McKarey-Kaufman, Optisol-GS or hyaluronic acid sodium salt medium. Clarity, thickness and endothelial cell mortality were evaluated at 3, 7 or 14 days and the results are reported in Table 3. Excellent cornea preservation was observed in Optisol-GS and hyaluronic acid medium. Even after 14 days the loss of endothelial cells did not exceed 7%. Staining with alizarin red and trypan blue at 7 days confirmed the integrity of endothelium. In agreement, corneal clarity and thickness were well preserved. In contrast, McKarey-Kaufman medium was less effective. Clarity started to be lost at day 3, whereas thickness was increased till a maximum of 40% at day 7. Endothelial cell loss reached 22–25% at day 14. These results confirmed the poor attitude of dextran to serve as a corneal preservative and indicated the greater effectiveness of both chondroitin sulfate and hyaluronic acid sodium salt. Hyaluronic acid sodium salt, however, was able to achieve satisfactory corneal preservation in the absence of dextran that is required in the Optisol-GS medium. AS stated above, dextran may penetrate the corneal tissue and may increase the swelling pressure upon rewarming.

Clinical studied: A group of eight patients scheduled for penetrating keratoplasty received corneas stored in the hyaluronic acid medium, a parallel group of eight patients received corneas stored in Optisol-GS. Re-epithelialization of corneas was completed in 3 days following surgery. After two weeks, clarity and thickness of corneas were well preserved. Analysis of endothelial cell density was performed in 10 patients and confirmed the effectiveness of two media. All grafts were in good conditions after two months when they showed re-epithelialization and grade 3 clarity (Table 4).

Conclusions

Overall, the results of our study demonstrate that hyaluronic acid is an effective agent for corneal preservation, even in the absence of other substances in the storage medium. Its main advantage is the effectiveness in the absence of other additions to the storage medium. This makes the composition of medium simple and inexpensive, avoiding complex nutrient mixture. Furthermore, the absence of labile components such as peptides or proteins (growth factors) increases the stability of the medium on storage and prevents the formation of degradation products. A further advantage of hyaluronic acid medium is to preserve a thin tissue at the time of surgical procedure. This allows an accurate evaluation of tissue conditions and easier handling during transplant.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

TABLE 1

CHARACTERISTICS OF THE MEDIUM CONTAINING HYALURONIC ACID SODIUM SALT, COMPARED WITH THOSE OF MK AND OPTISOL-GS ®

| COMPONENT OF FLUID | MK[1] | Optisol-GS ® | Medium containing hyaluronic acid sodium salt |
|---|---|---|---|
| MEDIUM | TC 199 | TC 199 Eagle's BSS MEM | TC 199 |
| BUFFER | HEPES 25 mM | HEPES 25 mM | HEPES 25 mM |
| BICARBONATE OF SODA | 0.35 g/L | unknown | 0.35 g/L |
| ANTIBIOTIC | Gentamycin 100 µg/ml | Gentamycin µg/ml Streptomycin 200 g/ml | Gentamycin µg/ml |
| HYALURONIC ACID SODIUM SALT | — | — | 2% |
| pH | 7.2–7.4 | 7.2–7.4 | 7.2–7.4 |
| OSMOLARITY | 310–330 mOsm/Kg | 320 mOsm/Kg | 330 mOsm/Kg |

[1]McKarey-Kaufman Solution comprised of dextran.

TABLE 2

PENETRATING KERATOPLASTY - DONOR CHARACTERISTICS

| Donor No. | Age (yrs) | Sex | Cause of death | Time lapse till explant (hrs/mins) | Endothelial density (cells/mm$^2$) |
|---|---|---|---|---|---|
| 1 | 79 | F | Cardiovascular disease | 4.20 | 2700 |
| 2 | 52 | F | Cardiovascular disease | 9.10 | 2600 |
| 3 | 61 | F | Tumour | 3.10 | 2200 |
| 4 | 50 | M | Cardiovascular disease | 2.10 | 2800 |
| 5 | 86 | M | Tumour | 2.10 | 2600 |
| 6 | 46 | F | Tumour | 2.00 | 3000 |
| 7 | 85 | F | Cardiovascular disease | 5.10 | 2400 |
| 8 | 55 | F | Cardiovascular disease | 3.30 | 2500 |

TABLE 3

RESULTS OF IN VITRO EXPERIMENTS
PAIRS OF HUMAN CORNEAS, PRESERVED IN MK, OPTISOL-GS,– (OPT) AND MEDIUM CONTAINING HYALURONIC ACID SODIUM SALT (HA)
ANALYSES ON DAYS 0, 3, 7 AND 14.

| Cornea | Donor age (yrs) | Death/ explant time lapse | Endothelial density (cells/mm$^2$) | Clarity 0 | 3 | 7 | 14 | Mean thickness (µm) 0 | 3 | 7 | 14 | Mortality in folds mean (%) 0 | 3 | 7 | 14 | Diffuse mortality mean (%) 0 | 3 | 7 | 14 |
|---|---|---|---|---|---|---|---|---|---|---|---|---|---|---|---|---|---|---|---|
| 1-MK | 45 | 5.00 | 2100 | 3 | 2 | 1 | — | 488 | 520 | 668 | — | 1 | 4 | 14 | — | 1 | 3 | 9 | — |
| 1-OPT |  |  |  | 3 | 3 | 3 | — | 500 | 481 | 487 | — | 1 | 3 | 5 | — | 1 | 1 | 2 | — |
| 2-MK | 89 | 5.00 | 1820 | 2 | 2 | 1 | — | 550 | 589 | 608 | — | 2 | 3 | 7 | — | 0 | 3 | 5 | — |
| 2-HA |  |  |  | 2 | 2 | 2 | — | 507 | 494 | 494 | — | 2 | 2 | 2 | — | 0 | 0 | 2 | — |
| 3-MK | 58 | 11.30 | 1600 | 2 | — | — | 1 | 485 | — | — | 695 | 5 | — | — | 22 | 0.5 | — | — | 25 |
| 3-HA |  |  |  | 2 | — | — | 2 | 464 | — | — | 380 | 5 | — | — | 7 | 0.5 | — | — | 1 |
| 4-OPT | 81 | 10.00 | 2400 | 3 | — | 2 | — | 475 | — | 475 | — | 7 | — | 8 | — | 0 | — | 1 | — |
| 4-HA |  |  |  | 3 | — | 2 | — | 500 | — | 469 | — | 2 | — | 3 | — | 0 | — | 1 | — |
| 5-OPT | 56 | 11.00 | 2500 | 3 | — | — | 2 | 510 | — | — | 440 | 3 | — | — | 6 | 0 | — | — | 3 |
| 5-HA |  |  |  | 3 | — | — | 2 | 486 | — | — | 450 | 1 | — | — | 5 | 0 | — | — | 2 |

TABLE 4

RESULTS OF PENETRATING KERATOPLASTY. PAIRS OF HUMAN CORNEAS PRESERVED IN OPTISOL-GS ® OR MEDIUM BASED ON HYALURONIC ACID SODIUM SALT
ND = NOT DETERMINED

| No. | Age (years) | Sex | Corneal Pathology | Storage time (hours) | Diameter of graft (mm) | Days after surgery | Riepithe-lization | Clarity | Pachymetry ($\mu$m) | Endothelial cell density (cells/mm$^2$) |
|---|---|---|---|---|---|---|---|---|---|---|
| 1-HA | 51 | M | Groenouw dystrophy | 47 | 8.0–8.2 | 14 | 2 | 2 | 540 | 2000 |
| 1-OPT | 28 | F | Keratoconus | 47 | 7.5–7.7 | 15 | 3 | 2 | 560 | 2000 |
| 2-HA | 50 | F | Post-herpetic leukoma | 26 | 8.0–8.2 | 16 | 3 | 3 | 550 | 2100 |
| 2-OPT | 36 | M | Post-herpetic leukoma | 25 | 8.0–8.2 | 16 | 2 | 3 | 560 | 2250 |
| 3-HA | 70 | M | Acquired endothelial dystrophy | 71 | 8.0–8.2 | 16 | 3 | 2 | 500 | 1220 |
| 3-OPT | 87 | M | Bullous keratopathy | 168 | 7.5–8.0 | 16 | 3 | 2 | 520 | ND |
| 4-HA | 66 | M | Post-traumatic leukoma | 96 | 9.1–9.5 | 13 | 2 | 2 | 568 | 2100 |
| 4-OPT | 43 | M | Keratoconus | 96 | 8.0–8.2 | 13 | 3 | 2 | 550 | ND |
| 5-HA | 26 | F | Keratoconus | 72 | 7.5–7.7 | 12 | 3 | 3 | 545 | ND |
| 5-OPT | 46 | F | Keratoconus | 72 | 8.0–8.2 | 13 | 3 | 3 | 520 | ND |
| 6-HA | 48 | F | Keratoconus | 72 | 8.0–8.2 | 10 | 3 | 3 | 533 | ND |
| 6-OPT | 25 | M | Keratoconus | 72 | 9.1–9.5 | 10 | 3 | 3 | 558 | ND |
| 7-HA | 32 | M | Keratoconus | 40 | 7.5–7.7 | 10 | 3 | 3 | 528 | 1200 |
| 7-OPT | 51 | F | Keratoconus | 40 | 7.5–7.7 | 10 | 3 | 3 | 555 | 1800 |
| 8-HA | 57 | M | Vascularized leukoma | 96 | 7.8–8.0 | 14 | 3 | 2 | 610 | 2400 |
| 8-OPT | 69 | M | Bullous keratopathy | 96 | 8.6–9.0 | 13 | 3 | 1 | 633 | 2200 |

What is claimed is:

1. A corneal storage solution which comprises hyaluronic acid sodium salt having an average molecular weight of 50,000 to 150,000 Da in a concentration of 1–2% weight/volume;

a balanced electrolyte solution;

and at least one antibiotic.

2. The solution of claim 1, wherein the pH of the balanced electrolyte solution is 7.2–7.4.

3. The solution of claim 1, wherein the antibiotic is at least one member selected from the group consisting of gentamycin; penicillin G, and streptomycin.

4. The solution of claim 1, wherein the concentration of the hyaluronic acid sodium salt is 1% weight/volume.

5. A method of storing corneal tissue which comprises exposing the corneal tissue to the solution of any one of claims 1–4.

6. The method of claim 5 wherein said solution is maintained at a temperature of 2–8° C.

* * * * *